(12) United States Patent
Kavteladze (10) Patent No.: US 8,343,210 B2
(45) Date of Patent: Jan. 1, 2013

(54) STENT AND STENT RETRIEVAL SYSTEM AND A METHOD OF PULLING A STENT INTO TUBULAR MEMBER

(75) Inventor: Zaza Alexandrovich Kavteladze, Moscow (RU)

(73) Assignee: Stenz Corporation, Wilmington, DE (US)

( * ) Notice: Subject to any disclaimer, the term of this patent is extended or adjusted under 35 U.S.C. 154(b) by 540 days.

(21) Appl. No.: 11/597,759

(22) PCT Filed: May 25, 2005

(86) PCT No.: PCT/DK2005/000345
§ 371 (c)(1),
(2), (4) Date: Jul. 1, 2008

(87) PCT Pub. No.: WO2005/115273
PCT Pub. Date: Dec. 8, 2005

(65) Prior Publication Data
US 2008/0281403 A1 Nov. 13, 2008

(30) Foreign Application Priority Data
May 25, 2004 (EP) .................................. 04388036

(51) Int. Cl.
*A61F 2/06* (2006.01)
(52) U.S. Cl. ..................................................... 623/1.16
(58) Field of Classification Search .................. 606/108, 606/194, 200; 623/1.15, 1.16, 1.18, 1.19, 623/1.2
See application file for complete search history.

(56) References Cited

U.S. PATENT DOCUMENTS

| | | | |
|---|---|---|---|
| 5,928,280 A | 7/1999 | Hansen et al. | |
| 5,968,088 A | 10/1999 | Hansen et al. | |
| 6,383,216 B1 | 5/2002 | Kavteladze et al. | |
| 6,485,507 B1 | 11/2002 | Walak et al. | |
| 6,506,411 B2 * | 1/2003 | Hunter et al. | 424/501 |
| 7,048,014 B2 * | 5/2006 | Hyodoh et al. | 140/92.1 |
| 7,799,050 B2 * | 9/2010 | Hensley et al. | 606/200 |
| 2001/0032010 A1 | 10/2001 | Sandock | |
| 2002/0143387 A1 | 10/2002 | Soetikno et al. | |

FOREIGN PATENT DOCUMENTS

| | | |
|---|---|---|
| EP | 1097728 A | 5/2001 |
| EP | 0744164 B | 9/2003 |

OTHER PUBLICATIONS

Merriam-Webster definition for "connection"; http://www.merriam-webster.com/dictionary/connection.*
Merriam-Webster definition for "interconnection"; http://www.merriam-webster.com/dictionary/interconnection.*
Solitaire Flow-Restoration Device for Treatment of Acute Ischemic Stroke: Safety and Recanalization Efficacy Study in a Swine Vessel Occlusion Model. AJNR Am J Neuroradical,. Jul. 15, 2010, 10.3174/anjr.A2169.

* cited by examiner

*Primary Examiner* — Ryan Severson
*Assistant Examiner* — Jonathan W Miles
(74) *Attorney, Agent, or Firm* — Haugen Law Firm PLLP (57) ABSTRACT

A stent has an engagement member (9). A stent retrieval system has a tubular member (13) and a retrieval member (14) with an engagement means (15). The engagement member is attached to an end row of cells of the tubular stent body (1). The cells in one annular row of cells are interconnected with the subsequent row of similarly oriented cells (2a) at areas of interconnection (7) which in the subsequent annular row of cells are circumferentially offset with respect to the connections (8) between the cells in said subsequent annular row of cells.

16 Claims, 3 Drawing Sheets

STENT AND STENT RETRIEVAL SYSTEM AND A METHOD OF PULLING A STENT INTO TUBULAR MEMBER

The present invention relates in a first aspect to a stent and a stent retrieval system, said retrieval system comprising a tubular member with a lumen terminating in a distal end opening, and a retrieval member with at least one engagement means, the tubular member and the retrieval member being mutually axially displaceable while the retrieval member extends in said lumen of the tubular member, said stent comprising at least one engagement member to which said at least one engagement means can engage and a tubular body of a plurality of annular rows of cells that are interconnected and located one after the other in the axial direction of the tubular body, the cells in one annular row of cells being interconnected with the subsequent row of similarly oriented cells at areas of interconnection which in said sub-sequent annular row of cells are circumferentially offset with respect to the connections between the cells in said subsequent annular row of cells.

Such a stent and a stent retrieval system is known from WO 2004/008991 disclosing a stent having in one end larger cells that are not arranged in annular rows but instead in rows extending over only one side of the stent. The cells in this end structure have been given a more coarse structure, and in the end row there is only a single cell into which an engagement member can engage.

U.S. Pat. No. 5,643,309 describes a stent provided with a number of inward projecting hooks at a distance from each end of the stent. The stent retrieval system comprises an outer sheath and a tubular member with an engagement ring fixed to carrier legs on the outside of the tubular member, and an inner retrieval member provided displaceably in the tubular member. The retrieval member is also provided with an engagement ring fixed to carrier legs on the outside of the member. When the stent is to be removed from a vascular site, the sheath is introduced into the stent, and the tubular member and the retrieval member are both advanced out of the sheath and tubular member, respectively, so that both engagement rings are allowed to expand within the stent. The two engagement rings are brought into engagement with the two sets of hooks on the stent, and then the tubular member and the retrieval member are moved in opposite directions so that the stent is pulled out to a longer length by the action of the rings on the hooks. Due to the elongation of the stent its diameter is reduced to such an extent that the stent is released from the vascular wall, and then the stent is pulled out. The system is complicated and difficult to use.

EP 0 829 242 A1 and US 2002 0120277 A1 both describe a stent retrieval system comprising a tubular member with a lumen terminating in a distal end opening, and a retrieval member with a plurality of engagement means shaped as tines with outward open hooks that after introduction to a position inside the stent can be moved radially outwards into the wire mesh of the stent. When the retrieval member is withdrawn the hooks engage in the wire mesh and pulls the stent out to a longer length. As the stent is pulled longer its diameter is reduced. The combined pulling action and diameter reduction acts to tear the stent loose from the vascular wall.

In U.S. Pat. No. 5,910,144 a plurality of gripper elements can be moved to the position of a stent and be allowed to radially spread out to a larger diameter than the stent diameter so that the gripper elements can be pushed in on the outside of the stent. Then the grippers are moved radially together so that the stent is compressed to a smaller diameter and can be pulled out.

It is in the first aspect of the present invention an object of the invention to obtain a stent and a stent retrieval system providing a more secure retrieval of the stent.

To meet this object the stent and stent retrieval system is characterized in that the end row of cells is an annular row of cells comprising first cell sides forming at least one circumferentially closed loop in which the individual cell has an attachment point, that said at least one engagement member comprises at least three tie members that are mutually connected at a junction and extend individually from the junction to the attachment point of an associated cell, and that the attachment points in the annular end row of cells are circumferentially offset with respect to the connections or areas of interconnection at the end of the tubular body between the cells in said end row.

The at least three tie members in the engagement member provide a firm and suitably distributed grip in the first row of cells at the end of the tubular body so that the cells are folded in a symmetrical manner. By attaching the engagement member to the annular end row of cells at points that are circumferentially offset with respect to the connections between the cells in the row, a pulling action in the engagement member will cause deformation of the cell sides extending between the individual attachment point and the adjacent connections between cells. The initial pull draws the engagement member towards the tubular member and into abutment with the distal end opening thereof, and during further pulling the engagement member is pulled into the lumen of the tubular member and the end row of cells is brought to abutment with the rim of the opening. As the engagement member is pulled into the lumen it acts on the end row of cells and cause some deformation thereof. As these deformations act locally and only to the end side of the annular row of cells, that row of cells will radially collapse to a smaller diameter at the end side, but remain at almost the initial diameter at the opposite side of the annular row. It is an advantage that the tie members extend individually to the attachment points because this on the one hand minimizes any obstructing effect from the tie members on the flow in the vascular vessel as any filtering effect or the like on the flow in the vessel is highly undesired, which could easily have occurred had the tie members been inter-connected in between the junction and the attachment points, and on the other hand any pull at the junction is automatically evenly balanced between the tie members when they extend individually to the attachment points.

The collapsed end side can be drawn radially down towards and into the distal end opening by pulling in the engagement member. As this is done, the cell sides in the end row of cells are turned and/or bend inwards in an angle that increases as the end side is pulled down to a smaller diameter. This pattern of movement of cell sides is very advantageous, especially when the stent is to be removed from a vascular site where it has been temporarily positioned for a desired period of time, because only minimum damage is done to the vascular wall.

When a stent is placed in a vessel, e.g. a blood vessel, tissue will within few days be formed around the stent material. Such ingrowth of tissue makes the stent become an integral part of the vascular wall. The ingrowth results in a layer of tissue, called intima, on the inside of the stent. If a stent is removed by using the prior art techniques of stent removal where the diameter of the stent is reduced by pulling the whole stent out to a longer length the tearing loose from the intima acts along a large area of the vascular wall, and the risks of damaging the vascular wall are high. If the vessel is weak, which is often the case in places where a stent is utilized, there is even a quite high risk of tearing the vessel apart when the stent is removed. With the pre-sent invention it has been recognized that the tearing apart can be caused by an axially directed pull in the stent in conjunction with a radial contraction that acts along a substantial length of the stent.

The stent according to the present invention is not subjected to any substantial axial pull during removal. The pulling in the engagement member only needs to be sufficient to pull down one side of one annular row of cells. When this pulling is effected the vascular wall remains supported by all remaining cells in the annular rows that have not yet been moved into the tubular member. The stent is thus kept axially stationary with respect to the parts of the vascular wall being in contact with the stent. The annular row of cells which is in the process of being pulled radially down into the tubular member is released in a gentle manner from the vascular wall. This is so, because only one side of the row is initially moved free of the vascular wall, and then the cell material is gradually moved free in direction of the other side of the row due to the cell material turning or bending inwards in the vessel. When one side of the annular row has been moved into the distal end opening, the tubular member is pushed forwards in direction of the other side of the annular row located at the subsequent annular row of cells.

During this pushing of the tubular member the cell material enters the distal end opening and then the other side of the annular row is pulled down to a smaller diameter and in doing so the cell material is moved radially inwards and out of the vascular wall. Then the process is repeated with the subsequent annular rows of cells. The areas of interconnection between one row and the subsequent row are offset in the circumferential direction with respect to the connections between the cells in the subsequent row. A pulling action in interconnections will cause deformation of the cell sides extending between the individual attachment point and the adjacent connections between cells. As these deformations act locally and only to the end side of the annular row of cells that row of cells will radially collapse to a smaller diameter at the end side, but remain at almost the initial diameter at the opposite side of the annular row. Then the tubular member can be pushed forward to the next annular row. The procedure is repeated until the stent has been placed completely within the tubular member, and then the retrieval system is withdrawn from the vascular system.

From the above explanation it follows that the cell material of the stent is released from the vascular wall by effecting radially acting local pulls in the cell material anchored in the vascular wall so that the cell sides are moved towards the centre line of the tubular body during the release from the vascular wall, and the radially directed pulling forces act symmetrically on the tubular body in the circumferential direction. The pulling forces furthermore only act on the annular row of cells that are in the process of collapse. The cells in the tubular body located more than one annular row of cells away from the collapsing cells are consequently unaffected by the forces used to collapse cells.

Also the annular end row of cells is released from the vascular wall by mainly radially acting forces caused by the engagement member being drawn in through the distal end opening of the tubular member. The tie members collectively and simultaneously act on the attachment points in all cells in the end row when the engagement member is moved into the lumen of the tubular member. The tie members extend directly from the common junction to their individual attachment point on the cell to which the individual tie member is connected.

The stent retrieval system can also be utilized to position a stent in the tubular member from an unloaded stent condition before the stent is introduced into a patient. The retrieval system can in other words be used as a system for loading a stent into a tubular member, e.g. an introducer system.

In an embodiment the individual attachment point is circumferentially located approximately at the middle between the two adjacent connections. With such a location the cells in the end row will collapse evenly about the attachment points. It is of course also possible, but not preferred, to position the attachment points in an asymmetric manner with respect to the adjacent connections.

In another embodiment the individual area of interconnection to a subsequent annular row is circumferentially located approximately at the middle between the two adjacent connections. With this location the cells in the subsequent row will collapse evenly about the areas of interconnection. It is of course also possible, but not preferred, to position the areas of interconnection in an asymmetric manner with respect to the adjacent connections.

In a preferred embodiment the first cell sides extending from the individual attachment point form mutually on the side of the attachment point an angle ($\delta_1$) of less than 176°. As a consequence of this design the first cell sides have to be raised through the angle of 180° before end cells in the end row begin to collapse. During this movement the diameter of the end of the tubular body is slightly increased and this causes some resistance which allow the engagement member to be drawn partly into the distal end opening and said end opening to be pushed closer towards the end row so that the tie members are oriented more radially, or in mainly radial directions, in areas adjacent the attachment points before the cells in the end row are brought to collapse. This design enhances the effect of causing radial directed pulls in the cell sides during release of the cell sides from the vascular wall.

In an embodiment the same principle is utilized in the internal rows of cells in the tubular body, in that the individual annular rows of cells located within the tubular body the first cell sides from at least one circumferentially closed loop in which the first cell sides extending from the individual area of interconnection form mutually on the side facing the end row with the attachment points an angle ($\delta_2$) of less than 176°. This embodiment can be used either in conjunction with the just mentioned design of the annular end row or on its own if the increased resistance against pulling down the annular end row is considered undesirable. In any case, in this embodiment the second cell sides will during their being pulled into the tubular member act as described above in connection with the tie members so that they will be oriented more radially, or in mainly radial directions, in vicinity of the areas interconnection just before the cells in the subsequent row are brought to collapse.

In a preferred embodiment the first cell sides in the individual annular row of cells form at least one circumferentially closed loop in which said first cell sides constituting the loop extend in directions forming angles in the range from 60° to 120° with the axial direction of the tubular body, when the tubular body is in an unloaded state. The closed loop provides the stent with high stiffness against radial compression and thus good properties for keeping a vessel patent, even at locations where the vessel exhibits a bend, but more importantly the closed loop has a high ability of maintaining its initial diameter when a local pull is performed in adjacent cell material. If the angle deviates well above 30° from 90° the tendency of maintaining the initial diameter can become feeble. It is preferred that the angular range is in the range from 70° to 110°, because the annular row of cell will then only to a small extent obtain a larger diameter when the first cell sides are pulled in direction of the distal opening. If the angular range is limited to the range from 75° to 105° the pull in the engagement member can be kept more constant.

In an embodiment second cell sides in the individual annular row of cells interconnect the circumferentially closed loops and extend at least along part of their length in directions forming angles in the range from 20° to 70° with the axial direction of the tubular body, when the tubular body is in an unloaded state. The flexibility of the second cell sides and the width of the individual annular row are comparatively well balanced when the angles are within the stated range. The range is preferably from 30° to 60°.

Preferably, said first cell sides extend substantially in a radial plane at the distal end opening of the tubular member, when said second cell sides in the adjacent annular row of cells have been pulled in through the distal end opening to extend from said distal end opening and into the tubular member. When the first cell sides can turn or flex to extend in or approximately in a radial plane when the second cell sides have been pulled through the distal end opening then the tubular body can maintain its initial diameter for as long time as possible.

It is preferred that the outer diameter of the subsequent loop outside the tubular member remains mainly unaffected while a loop is pulled into the distal end opening. As the subsequent loop is not affected the vascular wall at the subsequent loop is neither affected.

The junction of the engagement member is preferably located at the longitudinal central axis of the tubular body. By locating the junction at the central axis establishment of the engagement between the engagement means and the engagement member is more easily accomplished. The pull in the engagement member is also more evenly distributed to the attachment points when the junction is located at the central axis where the junction is symmetrically positioned with respect to the end row of cells.

In a most preferred embodiment the tie members a length so that the junction is located at least 0.5×W away from the annular end row of cells at the end of the tubular body, W being the width in the axial direction of the annular row of cells. By positioning the junction at such a distance from the end loop, this loop is more easily subjected to mainly radially acting forces when the junction is pulled in through the distal end opening because the length of the tie members assists to the bending of the tie members in the area in front of the distal end opening before the tie members are pulled completely into the lumen. The bent tie members will gradually pull the attachment points radially inwards as the tubular member is pushed in direction of the end loop, until the attachment points are located at the distal end opening with a mutual radial separation corresponding to the inner diameter of the lumen in the tubular member. This embodiment can be utilized on its own or in conjunction with the above mentioned embodiment where the first cell sides form an angle of less than 180° on the side facing the attachment point to which the first cell sides are connected.

In an embodiment the at least one engagement member comprises magnetic material. The engagement member can e.g. be of a ferromagnetic material which can attract a magnet, or it can be a magnet with a polarity facing in a certain direction, such as in the axial direction or the radial direction of the tubular body. In case the magnetic material has a polarity, this polarity can be opposite to the polarity of a magnetic material located on the engagement means so that the engagement means is attracted to the engagement member. Such an attraction effect can also be obtained with a magnet on one of the engagement member and the engagement means, when the other of the two parts is of a ferromagnetic material. The purpose of the magnetic materials is to facilitate the establishment of the engagement grip in the engagement member when this is located inside a vessel.

The inner lumen of the tubular member can have a diameter in the range from 20% to 80%, preferably from 30% to 60%, of the outer diameter of the tubular body in the unloaded state of the tubular body. Although it is possible to use a tubular member with a lumen of less than 20% of the outer diameter of the tubular body, there is not obtained any advantage by this, but to the contrary the lumen gets so diminutive that is may be more difficult to receive the tubular body in the lumen. The upper limit of 80% is sufficient to obtain full release of the stent from the tubular wall. The preferred range from 30% to 60% entails the advantages of providing more space in the lumen and a comparatively small outer diameter of the tubular member, thus facilitating the introduction of the stent retrieval system through the vascular system to the stent position.

In an embodiment the tubular body is provided with at least one additional means selected from the group consisting of a medically active substance, a bioactive factor inhibiting proliferation of a tumor cell, a bioactive substance, a bioactive agent, a drug, and a coating layer for controlled release of one or more of a bioactive material, a medically active substance or a bioactive factor. The bioactive substance or agent can e.g. be of a kind that reduces negative influences from the stent on the vascular wall or of a kind that enhances the effects of placing a stent in the vascular system. Alternatively the stent can be utilized as a carrier for introducing the said substance, agent, factor or drug to a vascular site where localized release of said substance, agent, factor or drug is desired. The stent is kept in place in the vascular system in the period required for obtaining the desired release of the substance, agent, factor or drug at the vascular site, and then the stent is removed by using the stent retrieval system. The stent retrieval system is in particular advantageous for such use, because of the very gentle removal procedure where the stent material is released from the vascular wall without or almost without subjecting the vascular wall to substantial forces directed in the axial direction of the tubular body. The annular rows of cells are individually released from the vascular wall by the mainly radial collapse of the rows. The vascular wall is quite often very weak at the locations where local release of drugs etc. is required. The weakening can e.g. be caused by the presence of tumor cells in vicinity of the vascular wall. Because of the gentle removal of the stent the risks of damaging the vascular wall by the removal are reduced to a minimum. It is consequently possible to treat even quite weak vascular sites with a temporary stent, which has hitherto not been possible.

In an embodiment said additional means has a predetermined active period in the range from three days to one month, preferably from 5 to 14 days. Ingrowth of an intima layer on the inside of the stent will increase with the duration of the placement. Due to the gentle removal of the stent it becomes possible to treat the vascular site for a longer period, such as up to one month, and yet remove the stent without inflicting intolerable damage to the vascular site.

It is possible to provide the tubular body with a tubular covering, such as a weave of graft material. The covering can serve to provide the stent with a large surface area, which can be an advantage, inter alia in cases where larger amounts of a drug or a bioactive substance or agent needs to be introduced to the vascular site. The covering can also be required in order to obtain temporarily closure of a branch vessel, an aneurysm or another vascular malformation.

In another aspect the present invention relates to a method of pulling a stent into a tubular member, the stent comprising at least one engagement member and a tubular body having a plurality of annular rows of cells that are interconnected and located one after the other in the axial direction of the tubular body, where at least one engagement means grips the at least one engagement member and pulls it through a distal end opening of the tubular member and into an inner lumen of said tubular member, said annular rows of cells having an initial diameter which is larger than the diameter of said inner lumen. Such a method is known from the abovementioned U.S. Pat. No. 5,643,309.

In relation to this second aspect the object of the invention is to load a stent into a tubular member in a simple manner and without use of complicated additional equipment.

With a view to this the method is characterized by pulling said at least one engagement member into and along the lumen of the tubular member and pushing the tubular member towards the tubular body, whereby the annular rows of cells are brought towards the end opening and are collapsed one-by-one at the end opening to a state with a radially reduced diameter, while the annular rows of cells maintain their initial diameter at least until they are within one row from said end opening.

The forces required to move the stent into the tubular member are quite low because the forces act mainly on the annular row of cells positioned immediately in front of the tubular opening. When cell sides in the annular row are pulled against the rim of the opening these cell sides deflect under the action of the rim to be oriented towards the inner lumen in the tubular member. During the continued pull in the engagement member the cell sides re-orient themselves at the radially reduced diameter corresponding to the inner lumen in the tubular member. Then the tubular member can be pushed towards the stent so that the rim of the end opening is moved towards the other side of the annular row of cells. During this movement the inner cell sides in the annular row are brought into the lumen, and because of the smaller diameter of the lumen these inner cell sides effect an increasingly strong radially directed pull in the cell sides at the opposite side of the annular row of cells so that these cell sides come to extend from the next annular row of cells at the initial diameter of the stent and inwards to radially more closely spaced locations at the end of the inner lumen of the tubular member. Then the procedure can be repeated with the next annular row of cells.

As there is no need for using complicated equipment in order to load the stent into the tubular member by the method of the present invention the loading can be performed shortly before the stent is to be used. This provides the substantial advantage of allowing a preparation of the stent with a coating having active properties of time-limited effect. If the active property of the coating only lasts for e.g. 7 or 14 days then the effects are lost during shelving of manufactured stents. By applying the coating to the stent shortly before the stent is to be used, and by loading the coated stent into the tubular member in the abovementioned manner, the stent is ready for use without any decay of the active property.

The invention will be explained in detail in the following by means of examples of embodiments with reference to the schematic drawing, in which.

Figure 1:
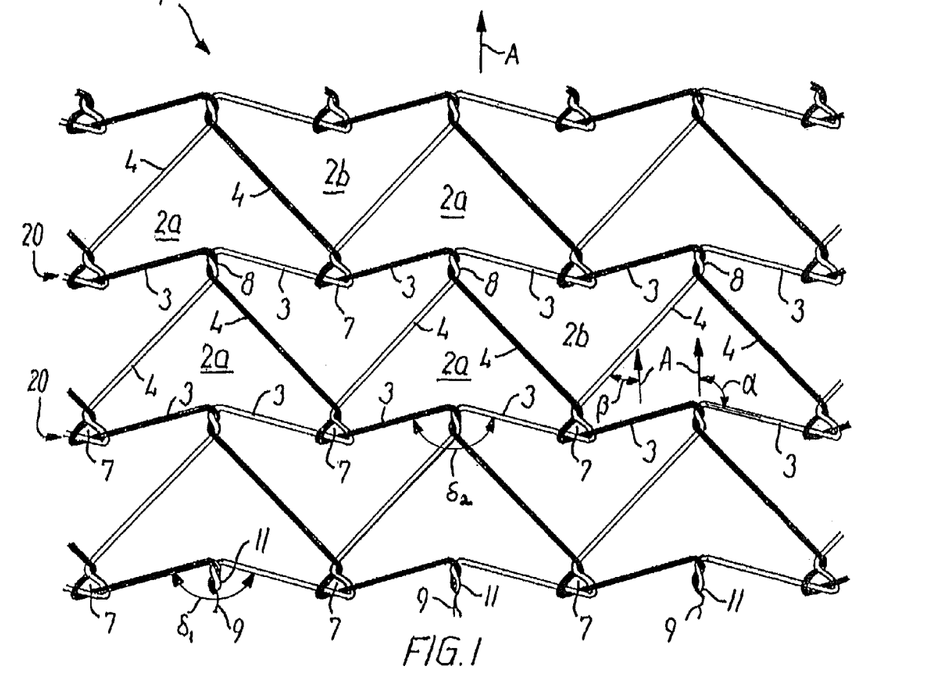
FIG. 1 is a plane view to illustrate the cell structure used in an embodiment of a tubular body of a stent according to the invention.
Figure 2:
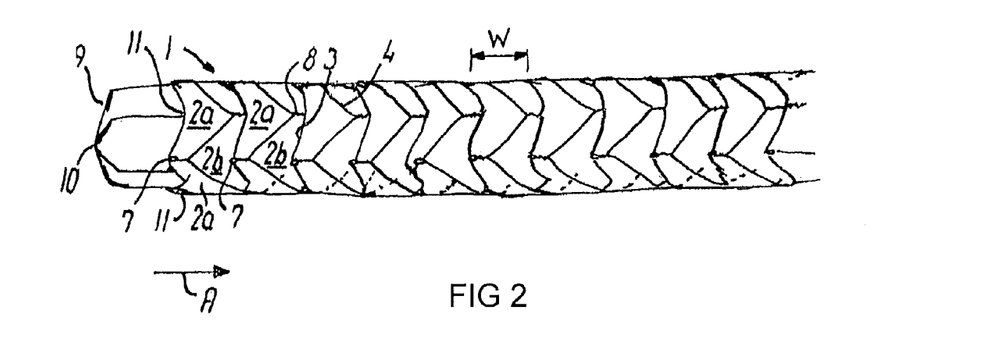
FIG. 2 depicts a side view of the stent having a cell structure as illustrated in FIG. 1, FIG. 3a to 3e show side views of sequential steps of the stent of FIG. 2 being pulled into a tubular member by use of a retrieval system.

FIGS. 1 and 2 illustrate the structure of a stent according to the invention, the stent being in an unloaded state. The stent is made up of wires that are bent or wound in a pattern to form a tubular body 1, see FIG. 2. For the sake of ease the cell pattern is illustrated in FIG. 1 in a cut up, unfolded state of the stent. The pattern is formed by annular rows of arrow-head-shaped or heart-shaped cells 2a, the rows being interconnected and arranged one after the other in the axial direction A of the tubular body 1. The annular rows of cells 2a have the same orientation in the tubular body. In between these rows of cells there are cells 2b having the opposite orientation in the axial direction, viz. the arrow-head or heart point in the opposite direction.

The tubular body is cylindrical in the unloaded state, and consequently all the annular rows, including the annular end row of cells are capable of expanding into contact with the vascular wall, and preferably the annular end row has the same diameter as the subsequent rows when the tubular body is in the unloaded state, but it can alternatively also have a larger diameter than the subsequent annular row.

Each cell 2a has two first cell sides 3 converging towards one another to become mutually connected in an area of interconnection 8 between the cells 2a in one row and the cells 2a in the subsequent annular row. The first cell sides 3 form at either end side of the annular row of cells a circumferentially closed loop 20 in which the first cell sides extend at an angle α of approx. 107° with respect to the axial direction A. On the side facing the area of interconnection the two first cell sides 3 extending from the area of interconnection 8 consequently form an angle $\delta = 360° - 2 \times \alpha = 146°$. Each cell 2a also has two mutually converging second cell sides 4 converging towards one another to become mutually connected in connections 7 between the cells 2a in the annular row. The second cell sides 4 interconnect the loops 20 at either side of the annular row of cells 2a. The second sell sides 4 extend in directions forming an angle β of approx. 38° with respect to the axial direction A. In other embodiments the mentioned angles can take other values. The angle α can e.g. be in the range from 60° to 120°, and the angle β can e.g. be in the range from 20° to 70°. Preferably the angle $\delta_1$ or $\delta_2$ is less than 180°, and suitably less than 176°.

The cell sides 3 are positioned opposite to cell sides 4 of the same cell, and the cells 2a of each cell row are connected by means of connections 7 forming loop-shaped nodes. The areas of interconnection 8 interconnecting one annular row of cells with the next row of cells form a node made up by wires wound once around each other. In the embodiment shown, the connections 7 and areas of interconnection 8 are mutually circumferentially offset with a distance corresponding substantially to the circumferential extent of one of the cell sides 3.

FIG. 2 depicts the tubular body 1 of the stent. An engagement member 9 is attached to an end row 12 of cells located at the left end of tubular body 1. The engagement member 9 is formed by four tie members in the form of wire sections, which are connected to each other at a junction 10 located at the longitudinal central axis of the tubular body 1. The individual tie member is connected to the tubular body 1 at an attachment points 11, the attachment points 11 being circumferentially offset with respect to the connections 7 at the end of the tubular body 1 with a distance corresponding substantially to the circumferential extent of one of the first cell sides 3. This locates each individual attachment point 11 at the middle of the cells 2a between the two adjacent connections 7 in the annular row 12 of cells at the end of the tubular member 1. The tie members have a length so that the junction 10 is located approximately 1.0×W away from the loop of the end row 12 of cells at the end of the tubular body 1, W being the width of one row of cells in the axial direction of the tubular body. There is preferably one tie member extending from each attachment point to the central junction 10, and preferably each cell in the annular end row of cells has one attachment point.

FIG. 3a to 3d show sequential steps of the stent of FIG. 2 being pulled into a tubular member 13 of a retrieval system according to the invention. A retrieval member 14 is located displaceable within the lumen of the tubular member 13 and has a longer length than the tubular member so that it can extend out of both the distal end and also out of the proximal end wherefrom it can be manipulated. The retrieval member is provided with an engagement means in the form of a hook 15 at its distal end. The retrieval member is e.g. made of steel or another material of sufficient strength.

Figure 3A:
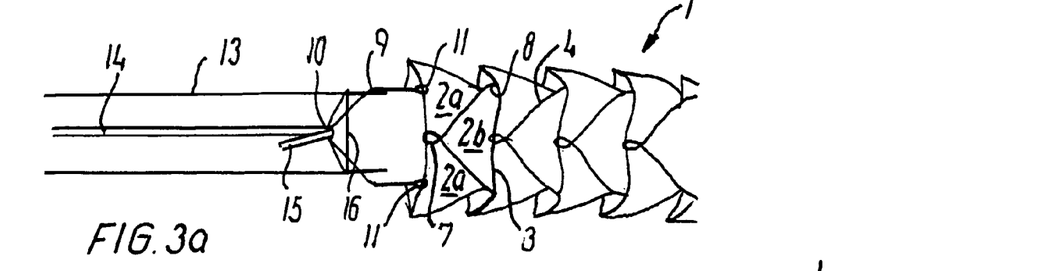

The tubular member 13 terminates at its distal end in a distal end opening surrounded by an annular end surface 16 on the tubular member. In the illustrated embodiment the diameter of the tubular member 16 corresponds to approximately 55% of the initial diameter of the tubular body 1 when the latter is in the unloaded (relaxed) state.

In FIG. 3a the retrieval member 14 of the retrieval system has engaged the tie members of the engagement member 9 at the junction 10 by means of the hook 15 being hooked around tie members. In the illustration the engagement member has been pulled towards the tubular member to the position in which the tie members abut the annular end surface 16 of the tubular member 13. The tubular body 1 is seen to still remain in its unloaded state.

Figure 3B:
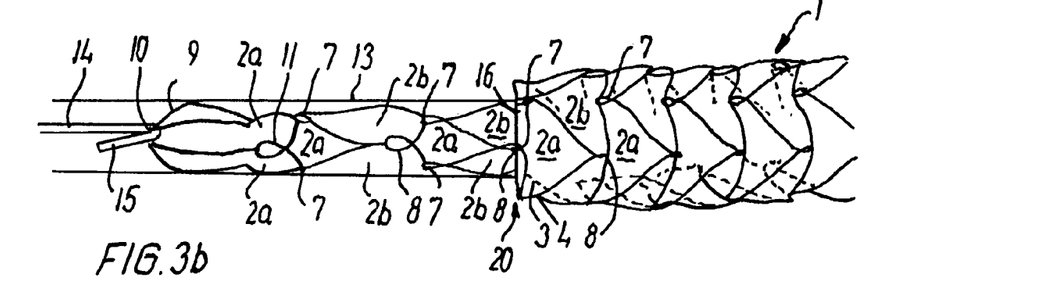
Figure 3C:
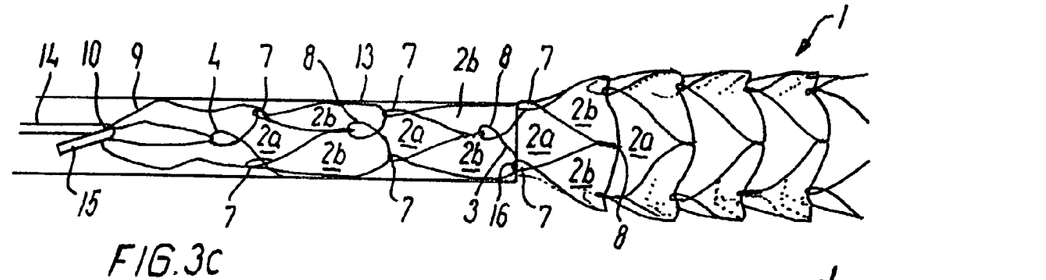

FIG. 3b to 3e show how the third row of cells is pulled into the tubular member 13. In FIG. 3b the hook 15 has pulled the engagement member 9 and two rows of cells into the tubular member 13 of the retrieval system, and the loop 20 at the proximal side of the third annular row of cells is located at the annular opening. The areas of interconnection 8 interconnecting the second and third rows of cells have been pulled inwards toward the central axis of the tubular body 1 and have just passed by the annular end surface 16 and entered the end opening of the tubular member 13. It is the second cell sides 4 of the second row of cells that have pulled the areas of interconnection of the second row of cells inwards towards the central axis of the tubular body 1, bending the first cell sides 3 of the third row of cells inwards.

As can be seen from the illustration in FIG. 3b, the second cell sides 4 of the third row of cells are slightly deformed. Thus, further pulling in the retrieval member 14 causes the first cell sides 3 and the connections 7 of the third row of cells to be radially drawn down to and pass in through the end opening of the tubular member 13, see FIGS. 3c and 3d. It should be noted that in FIGS. 3b to 3d the fourth row of cells remains unaffected of the collapse of the third row of cells and thus has not begun to collapse.

Figure 3D:
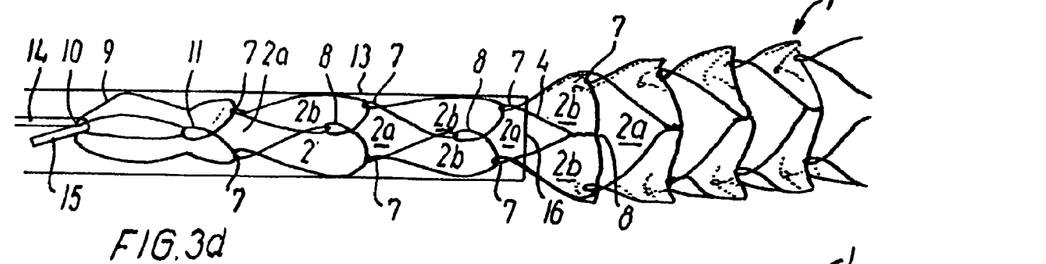

Once the connections 7 in the loop 20 at the proximal side of the third annular row have been drawn into the distal end opening of the tubular member, tubular body 13 can be displaced to the right hand side of the figure, viz. in direction of the tubular body. During this displacement of the tubular member the second cell sides 4 in the third annular row are moved into the lumen of the tubular member under concurrent diminishing of the diameter of the cells to correspond to the lumen.

Figure 3E:
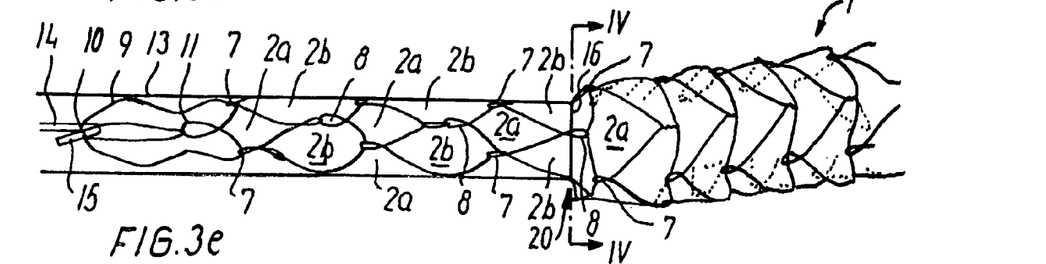

In FIG. 3e the tubular member has been advanced to be positioned with the distal end opening located near the proximal end loop 20 of the fourth annular row of cells, the first cell sides 3 of the fourth row of cells are bending inwards and are starting to pull the fourth row of cells into the tubular member 13. The process illustrated in FIGS. 3b to 3e with respect to the third row of cells is then repeated for the fourth row of cells, and similarly so forth for the subsequent rows of cells until the entire stent is located inside the tubular member.

Figure 4:
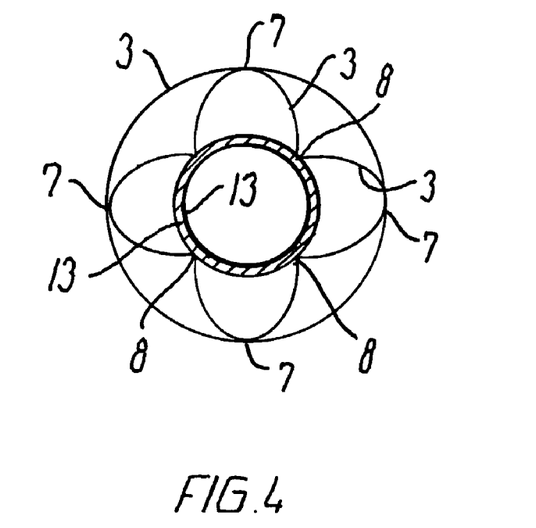
FIG. 4 shows a cross section along the line IV-IV of FIG. 3e viewed from the left side of FIG. 3e.

In FIG. 4 the initial collapse of the fourth row of cells is elaborated, the illustration showing a cross section along the line IV-IV of FIG. 3e viewed from the left of FIG. 3e. In FIG. 4 the first cell sides 3 of the proximal loop in the fourth row of cells are partially collapsed and extend from the areas of interconnection 8 inside the tubular member 13 and outwards to the connections 7. The first cell sides 3 of the fourth row of cells have been bend to form curved shapes forming a flower-like shape with four leaves. The fifth row of cells is still in its initial state, and the first cell sides 3 of the fifth row of cells extend along the contours of the larger outer circle of the illustration.

The engagement member on the stent can take other forms than the one illustrated in the above. It can e.g. be embodied in the form of several wires crossing each other, so that the junction 10 is formed of the wires inter-crossing one another, but the tie members are preferably joined at the junction, in particular if they are of a flexible material. The tie members can be embodied as flexible threads, or they can be embodied as loops or eyes or legs extending from the circumference of the end annular row of cells and radially or obliquely inwards towards the centre line of the tubular body. Preferably, only one tie member extends from the junction to the individual attachment point, but one or more of the attachment points can be connected to more than one tie member. The engagement member can comprise a magnet or magnetic material. The engagement means on the retrieval member can also be shaped with several hooks or it can include a gripper means, a tongue, an eye or a string to be fixed to the one or several engagement members on the tubular body. What matters is that the engagement means can be brought into a condition where the retrieval member can act with a pulling force distributed to the engagement points on the individual cells in the annular end row of the tubular body.

The length of the tie members can depart from the above mentioned length causing the junction 10 to be located approximately 1.0×W away from the loop of the end row 12. In one embodiment the length of the tie members correspond to half the diameter of the tubular body which causes the tie members to be radially directed towards the junction, but preferably the tie members are substantially longer. The tie members can also be pre-shaped to locate the junction asymmetrically with respect to the longitudinal central axis of the tubular body when there is no pull in the junction and of sufficient flexible construction to allow the junction to be centred once the engagement means establishes the pull in the engagement means. This embodiment can be advantageous when it is important to maintain the largest possible unobstructed flow area through the tubular body during the temporary placement thereof in the vascular vessel. In an embodiment where the tie members are of flexible thread of having an individual thread length of more than 1.0×W the tie members can be folded and temporarily mounted in a storage position on the end of the tubular body so that approximately the full lumen of the tubular body is unobstructed during the placement in the vascular vessel. When the stent is to be retrieved it is then required to loosen the folded up tie members so that they are only attached to the tubular body at the attachment points, before the engagement means can be brought in proper engagement with the engagement member.

Figure 5:
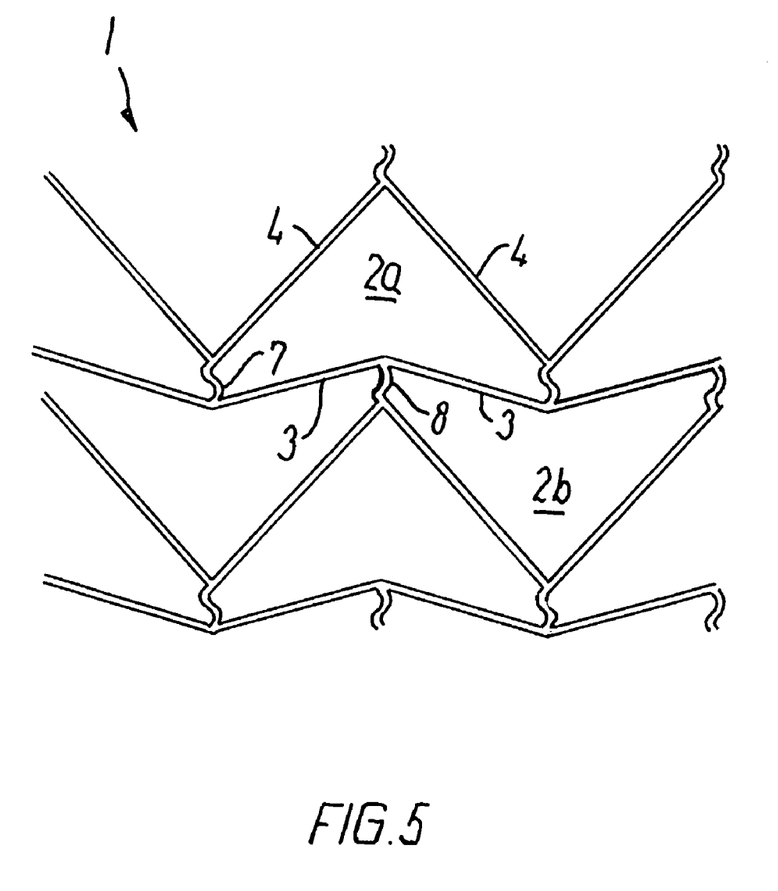
FIG. 5 shows a plane view corresponding to the view of FIG. 1 of another embodiment of a stent according to the invention made by laser cutting or etching in a tubular member.

FIG. 5 illustrates another embodiment of a stent according to the invention made by laser cutting or etching of a tubular member, the stent being in an unfolded state corresponding to FIG. 1 for the sake of illustration. In FIG. 5, parts similar to the previous illustrations have been given similar numerals. The operation of the embodiment of FIG. 5 corresponds substantially to the previously described embodiment. Thus, in the embodiment of FIG. 5 the connections 7 between the cells 2a, 2b and the points 8 of interconnection interconnecting subsequent rows of cells are formed as S-shaped joints. This makes said connections 7 and said interconnections 8 behave substantially similarly to the previously described embodiment. The cells in the tubular body can be of others cell patterns than the ones described. The cell sides can e.g. have an undulating run and they can have unequal widths or a width varying along the length of the cell side.

The number of cells in the individual annular rows of cells can vary depending on the actual cell shape and the diameter of the tubular body in its unloaded state. To give an example there can be four cells of even orientation in the annular row, but there can also be three cells or more than four, such as five, six or seven cells of the same orientation. Preferably the number of attachment points corresponds to the number of cells, and more preferably the number of tie members corresponds to the number of attachment points. However, if e.g. one or more of the cells are of weak or more open construction in comparison to the other cells it is possible to omit the attachment point on the weak cell.

The diameter of the tubular body in the unloaded state vary with the application of the stent. For use in arteries the stent can e.g. have a diameter in the range of 0.5 mm to 3 mm when it is to be placed in diminutive arteries or venes, such as in the brain, it can have a diameter in the range of 2 mm to 4 mm for coronary use or pancreatic uses, it can have a diameter in the range from 6 mm to 12 mm for iliac, femoral, renal and carotid uses etc.

The stent can also be provided with a covering on a part of or on the complete peripheral surface of the tubular body. The stent can be made of nitinol thread, such as a round or flat thread, or it can be of stainless steel, titanium, tantalum, platinum, composite materials or of synthetic materials.

In an embodiment the stent is provided with a bioactive material, such as heparin or another thrombin inhibitor, anti-inflammatory steroids including but not limited to dexamethasone and its derivatives, and mixtures of heparin and such steroids. The bioactive material or agent can also be an anti-proliferative agent such as methotrexate. The stent can e.g. be placed in the arterial supply of the tumor to provide a means of delivering a relatively high dose of the antiproliferative agent directly to the tumor. The bioactive material can furthermore be a vasodilator such as a calcium channel blocker or a nitrate. The stent can also be provided with a drug, such as an anti-cancer chemotherapeutic agent for delivery to a localized tumor, e.g. tamoxifen citrate, Taxol or derivatives thereof. Proscar®, Hytrin®, or Eulexin®. Dopamine or a dopamine agonist such as bromocriptine mesylate or pergolide mesylate can be mentioned as examples of drugs for other purposes. The stent can also be provided with a factor that exhibit anti-proliferative activity against cells. Such factors or compositions can e.g. be a cytotoxic/cytostatic, anti-proliferative factor. A pharmaceutically acceptable form of an anti-proliferative factor or a functional analog thereof can typically be used.

Details of the above mentioned embodiments can be combined into other embodiments within the scope of the appended claims. The cell shapes need not be of the particular type illustrated on the drawing, as the scope of the claims comprises other cell shapes, such as approximately rectangular cells, cells where the connections between the cells in the individual row of cells extend mainly or completely in the axial direction of the tubular body and the cell sides (the abovementioned first cell sides) forming circumferentially closed loops extend in directions forming angles of at least 92° or less that 88° with the axial direction of the tubular body. The cells can also be polygonal, such as hexagonal, or the first cell sides in the circumferentially closed loops can have a wavy shape or form a meander shape.

The invention claimed is:

1. A stent and stent retrieval system, said retrieval system comprising a tubular member with a lumen terminating in a distal end opening, and a retrieval member with a least one of engagement means, the tubular member and the retrieval member being mutually axially displaceable while the retrieval member extends in said lumen of the tubular member, said stent comprising at least one engagement member to which said at least one engagement means can engage and a tubular body of a plurality of annular rows of cells that are interconnected and located one after the other in the axial direction of the tubular body, the cells in one annular row of cells being interconnected with the subsequent row of similarly oriented cells at areas of interconnection which in said subsequent annular row of cells are circumferentially offset with respect to the connections between the cells in said subsequent annular row of cells, wherein the end row of cells is an annular row of cells comprising the first cell sides together forming at least one circumferentially closed loop in which the individual cell has an attachment point, wherein said at least one engagement member comprises at least three tie members that are mutually connected at a junction and extend individually from the junction to the attachment point of an associated cell, and wherein the attachment points in the annular end row of cells are circumferentially offset with respect to the connections or areas of interconnection at the end of the tubular body between the cells in said end row wherein, in the individual annular rows of cells located within the tubular body, the first cell sides together form at least one circumferentially closed loop in which the first cell sides mutually extending from the individual area of interconnection together form an angle ($\delta_1$) of less than 176° on an exterior of the respective cell associated with the individual area of interconnection.

2. A stent and stent retrieval system according to claim 1, wherein the individual attachment point is circumferentially located approximately at the middle between the two adjacent connections or areas of interconnection.

3. A stent and stent retrieval system according to claim 1, wherein the individual area of interconnection is circumferentially located approximately at the middle between the two adjacent connections.

4. A stent and stent retrieval system according to claim 1, wherein the first cell sides mutually extending from the individual attachment point together form an angle ($\delta_1$) of less than 176° on an exterior of the respective cell associated with the individual attachment point.

5. A stent and stent retrieval system according to claim 1, wherein in the individual annular row of cells the first cell sides form at least one circumferentially closed loop in which said first cell sides constituting the loop extend in directions forming angles (a) in the range from 60° to 120° with the axial direction (A) of the tubular body; when the tubular body is in an unloaded state.

6. A stent and stent retrieval system according to claim 1, wherein second cell sides in the individual annular row of cells interconnect the circumferentially closed loops and extend at least along part of their length in directions forming angles (β) in the range from 20° to 70° with the axial direction (A) of the tubular body when the tubular body is in an unloaded state.

7. A stent and stent retrieval system according to claim 1, wherein said first cell sides extend substantially in a radial plane at the distal end opening of the tubular member when second cell sides in an adjacent annular row of cells have been pulled in through the distal end opening to extend from said distal end opening and into the tubular member.

8. A stent and stent retrieval system according to claim 1, wherein while a loop is pulled into the distal end opening, the outer diameter of the subsequent loop outside the tubular member remains unaffected.

9. A stent and stent retrieval system according to claim 1, wherein said junction is located at the longitudinal central axis of the tubular body.

10. A stent and stent retrieval system according to claim 1, wherein the tie members have a length so that the junction is located at least 0.5×W away from the annular end row of cells, W being the width in the axial direction of the annular row of cells.

11. A stent and stent retrieval system according to claim 1, wherein said at least one engagement member comprises magnetic material.

12. A stent and stent retrieval system according to claim 11, wherein said magnetic material has a polarity which is opposite to the polarity of a magnetic material located on the engagement means.

13. A stent and stent retrieval system according to claim 1, wherein the inner lumen of the tubular member has a diameter in the range from 20% to 80% of the outer diameter of the tubular body in the unloaded state of the tubular body.

14. A stent and stent retrieval system according to claim 1, wherein the tubular body is provided with at least one additional means selected from the group consisting of a medically active substance, a bioactive factor inhibiting proliferation of a tumor cell, a bioactive substance, a bioactive agent, a drug, and a coating layer for controlled release of one or more of a bioactive material, a medically active substance or bioactive factor.

15. A stent and stent retrieval system according to claim 14, wherein said additional means has a predetermined active period in the range from three days to one month.

16. A stent and stent retrieval system according to claim 1, wherein the tubular body is provided with a tubular covering.

* * * * *

UNITED STATES PATENT AND TRADEMARK OFFICE
CERTIFICATE OF CORRECTION

PATENT NO. : 8,343,210 B2
APPLICATION NO. : 11/597759
DATED : January 1, 2013
INVENTOR(S) : Kavteladze Page 1 of 1

It is certified that error appears in the above-identified patent and that said Letters Patent is hereby corrected as shown below:

Column 13, line 3, replace "(A) of the tubular body;" with -- (A) of the tubular body --

Signed and Sealed this
Fifth Day of March, 2013

Teresa Stanek Rea
*Acting Director of the United States Patent and Trademark Office*